United States Patent
Kitahara

(10) Patent No.: US 12,237,073 B2
(45) Date of Patent: Feb. 25, 2025

(54) LEARNING DATA CREATION APPARATUS, METHOD, PROGRAM, AND MEDICAL IMAGE RECOGNITION APPARATUS

(71) Applicant: FUJIFILM Corporation, Tokyo (JP)

(72) Inventor: Masahiro Kitahara, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 767 days.

(21) Appl. No.: 17/114,451

(22) Filed: Dec. 7, 2020

(65) Prior Publication Data

US 2021/0201080 A1 Jul. 1, 2021

(30) Foreign Application Priority Data

Dec. 25, 2019 (JP) ................................. 2019-234770

(51) Int. Cl.
*G06T 7/00* (2017.01)
*G06F 18/214* (2023.01)
(Continued)

(52) U.S. Cl.
CPC ......... *G16H 30/40* (2018.01); *G06F 18/2148* (2023.01); *G06T 7/0014* (2013.01);
(Continued)

(58) Field of Classification Search
CPC ........ G16H 30/40; G16H 30/20; G16H 50/20; G16H 50/50; G06F 18/2148;
(Continued)

(56) References Cited

U.S. PATENT DOCUMENTS 10,813,541 B2 10/2020 Saito
10,860,930 B2 12/2020 Shiratani
(Continued)

FOREIGN PATENT DOCUMENTS

JP 2015112431 6/2015
JP 2016182161 10/2016
(Continued)

OTHER PUBLICATIONS

Zhang C et al, Real-Time Instrument Scene Detection in Screening GI Endoscopic Procedures, IEEE Symposium on Computer-Based Medical Systems, 1-6. (Year: 2017).*
(Continued)

*Primary Examiner* — Kathleen M Broughton
(74) *Attorney, Agent, or Firm* — JCIPRNET

(57) ABSTRACT

A learning data creation apparatus, a method, a program, and a medical image recognition apparatus are provided. The learning data creation apparatus includes a first processor, and a memory that stores learning data for machine learning. The first processor acquires a first medical image from a modality, detects each of a target region and a reference region from the acquired first medical image, determines whether or not the detected target region and the reference region are in contact, measures a size of the target region based on a size of the reference region in a case where a contact is determined, and stores, in the memory, as the learning data, a pair of the first medical image including the target region of which the size is measured, and the measured size of the target region.

13 Claims, 9 Drawing Sheets

(51) Int. Cl.
    *G06T 7/60* (2017.01)
    *G06V 10/22* (2022.01)
    *G06V 10/25* (2022.01)
    *G16H 30/20* (2018.01)
    *G16H 30/40* (2018.01)
    *G16H 50/20* (2018.01)
    *G16H 50/50* (2018.01)

(52) U.S. Cl.
    CPC ............... *G06T 7/60* (2013.01); *G06V 10/22* (2022.01); *G06V 10/25* (2022.01); *G16H 30/20* (2018.01); *G16H 50/20* (2018.01); *G16H 50/50* (2018.01); *G06T 2207/10068* (2013.01); *G06T 2207/20081* (2013.01); *G06T 2207/20084* (2013.01); *G06T 2207/30096* (2013.01); *G06V 2201/034* (2022.01)

(58) Field of Classification Search
    CPC ........... G06T 7/0014; G06T 7/60; G06T 7/62; G06T 2207/10068; G06T 2207/20081; G06T 2207/20084; G06T 2207/30096; G06V 10/22; G06V 10/25; G06V 2201/034; G06V 2201/031
    See application file for complete search history.

(56) References Cited

U.S. PATENT DOCUMENTS

| | | |
|---|---|---|
| 11,526,986 B2 | 12/2022 | Kamon |
| 11,556,731 B2 | 1/2023 | Nishimura |
| 2015/0313446 A1* | 11/2015 | Ogawa ............... A61B 1/00006 600/117 |
| 2016/0198982 A1* | 7/2016 | Cabiri ................ A61B 1/00096 600/476 |
| 2017/0150904 A1* | 6/2017 | Park .................... A61B 1/00009 |
| 2020/0279373 A1* | 9/2020 | Hussain ........... A61B 1/000096 |
| 2021/0158525 A1* | 5/2021 | Iwase ....................... G06T 7/11 |
| 2021/0257094 A1* | 8/2021 | Takemoto ............. G06T 7/0016 |
| 2023/0086972 A1 | 3/2023 | Kamon |

FOREIGN PATENT DOCUMENTS

| | | |
|---|---|---|
| KR | 102007656 B1 * | 8/2019 |
| WO | 2017175282 | 10/2017 |
| WO | 2019064704 | 4/2019 |
| WO | 2019138773 | 7/2019 |

OTHER PUBLICATIONS

Zhang C et al, Real-Time Instrument Scene Detection in Screening GI Endoscopic Procedures, 2017, IEEE Symposium on Computer-Based Medical Systems, 1-6. (Year: 2017).*

Iakovidis D et al, Deep Endoscopic Visual Measurements, 2019, IEEE Journal of Biomedical and Health Informatics, 23(6): 2211-2219. (Year: 2019).*

Thomas V et al, Training Data Enhancements for Robust Polyp Segmentation in Colonoscopy Images, 2019 IEEE 32nd International Symposium on Computer-Based Medical Systems, pp. 192-197. (Year: 2019).*

"Office Action of Japan Counterpart Application", issued on Apr. 7, 2023, with English translation thereof, p. 1-p. 6.

* cited by examiner

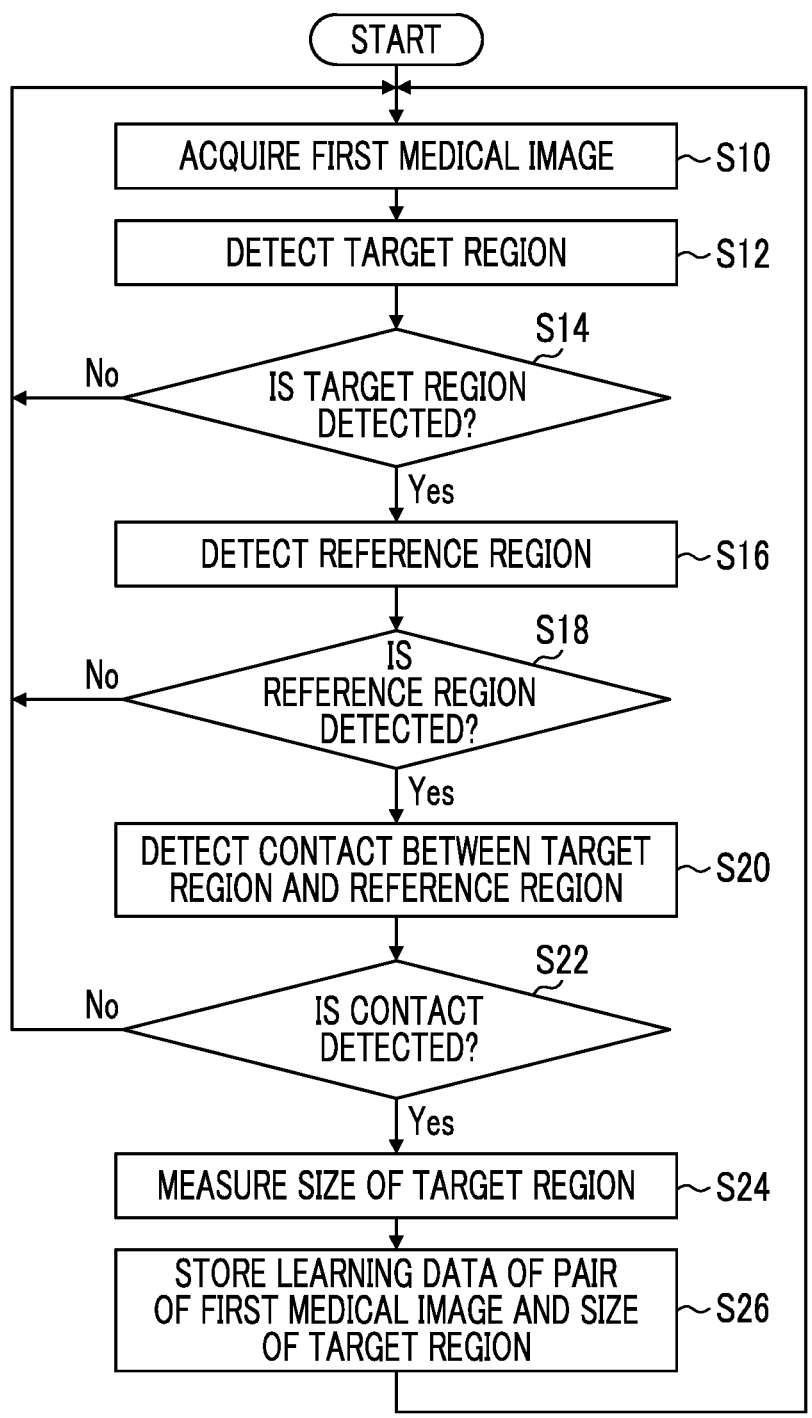

LEARNING DATA CREATION APPARATUS, METHOD, PROGRAM, AND MEDICAL IMAGE RECOGNITION APPARATUS

CROSS-REFERENCE TO RELATED APPLICATIONS

The present application claims priority under 35 U.S.C § 119 to Japanese Patent Application No. 2019-234770 filed on Dec. 25, 2019. The above application is hereby expressly incorporated by reference, in its entirety, into the present application.

BACKGROUND OF THE INVENTION

1. Field of the Invention

The present invention relates to a learning data creation apparatus, a method, a program, and a medical image recognition apparatus and particularly, to a technology for efficiently creating learning data with which machine learning is performed on a learning model.

2. Description of the Related Art

In recent years, a technology for supporting a test by recognizing a position of a lesion and a type of lesion included in a medical image such as an endoscopic image by image analysis and notifies a recognition result has been known.

In the image analysis for recognition, machine learning of an image including deep learning is widely used.

In a case of checking presence or absence of a focused region (target region) such as the lesion from the medical image, the target region exceeding a certain size (area) or larger may be resected. The target region less than a certain size may be preserved, and follow-up observation may be performed. In this case, the size of the target region needs to be accurately measured. However, a learning model on which machine learning processing is performed in order to measure (recognize) the size of the target region has not been known.

In the related art, a method of measuring the size of the target region by inserting measure forceps into a forceps port of an endoscope-scope, pressing gradations of a distal end portion of the measure forceps against the target region, and reading out the gradations has been known as a method of measuring the size of the target region in the endoscopic image.

In a case of the method of measuring the size of the target region using the measure forceps, the measure forceps needs to be inserted into the forceps port of the endoscope-scope for simply measuring the size of the target region, and a problem of inconvenience arises.

An endoscopic diagnosis apparatus disclosed in JP2016-182161A detects a region of an artificial object in contact with a test object from an endoscopic image, generates gradations representing an actual size of the test object on the endoscopic image based on an actual size (known size) of the region of the artificial object, and displays the generated gradations by compositing in the endoscopic image.

SUMMARY OF THE INVENTION

In the endoscopic image, the endoscopic diagnosis apparatus disclosed in JP2016-182161A composites the gradations created based on the size of the artificial object. Thus, while the "gradations" can be generated using the artificial object other than the measure forceps, the artificial object that has a known size and is in contact with the target region or a region in a vicinity of the target region needs to be captured in the endoscopic image.

A user needs to visually check the size of the target region by bringing the artificial object into contact with the target region of which the size is desired to be measured, or the region in the vicinity of the target region and reading out the gradations composited in the endoscopic image.

In a case of performing machine learning on a learning model in order to recognize the size of the target region, a large amount of learning data of a pair of a medical image in which the target region is captured, and the size (answer data) of the target region needs to be created. Generally, time and effort are taken to create the answer data in creating the learning data.

The present invention is conceived in view of such a matter, and an object thereof is to provide a learning data creation apparatus, a method, a program, and a medical image recognition apparatus capable of efficiently creating learning data for performing machine learning on a learning model that recognizes a size of a target region included in a medical image.

In order to achieve the above object, an invention according to a first aspect is a learning data creation apparatus comprising a first processor, and a memory that stores learning data for machine learning, in which the first processor acquires a first medical image from a modality, detects a target region from the acquired first medical image, detects a reference region having a known size from the acquired first medical image, determines whether or not the detected target region and the reference region are in contact, measures a size of the target region based on the size of the reference region in a case where a contact between the target region and the reference region is determined, and stores, in the memory, as the learning data, a pair of the first medical image including the target region of which the size is measured, and the measured size of the target region.

According to the first aspect of the present invention, the target region such as a lesion and the reference region having the known size are detected from the first medical image. In a case where it is determined that the detected target region and the reference region are in contact, the size of the target region is automatically measured based on the known size of the reference region. The pair of the first medical image including the target region of which the size is measured, and the measured size of the target region is stored in the memory as the learning data for performing machine learning on a learning model. Accordingly, the learning data is automatically accumulated in the memory, and a data set for machine learning of the learning model is obtained.

In the learning data creation apparatus according to a second aspect of the present invention, the first processor stores, in the memory, the first medical image constituting the pair as input data and stores the size of the target region as answer data.

In the learning data creation apparatus according to a third aspect of the present invention, it is preferable that the reference region is a region in which an artificial object is imaged.

In the learning data creation apparatus according to a fourth aspect of the present invention, it is preferable that the artificial object is a treatment tool. Examples of the treatment tool include not only biopsy forceps, measure forceps, a puncture needle, and a high-frequency knife but also a distal end hood attached to a distal end of an endoscope-scope.

In the learning data creation apparatus according to a fifth aspect of the present invention, it is preferable that in a case where a contact between the target region and the artificial object is detected based on image feature amounts of the target region and the reference region, the first processor determines that the reference region is in contact with the target region.

In the learning data creation apparatus according to a sixth aspect of the present invention, it is preferable that in a case where a detection signal indicating a contact between the target region and the artificial object is input from a contact sensor that is arranged at a distal end of the artificial object and detects the contact, the first processor determines that the reference region is in contact with the target region.

In the learning data creation apparatus according to a seventh aspect of the present invention, the first processor stores, in the memory, the learning data of a pair of the first medical image, among the first medical images, in which the contact between the target region and the reference region is determined, and the measured size of the target region. In this case, the first medical image includes the target region and the reference region.

In the learning data creation apparatus according to an eighth aspect of the present invention, it is preferable that the first processor acquires a time series of the first medical images, and stores, in the memory, the learning data of a pair of the first medical image, among the time series of the first medical images, that is captured before or after the first medical image in which the contact between the target region and the reference region is determined and that includes the same target region as the target region included in the first medical image in which the contact is determined, and the measured size of the target region.

In this case, the first medical image in which the reference region is significantly spaced from the target region, or the first medical image not including the reference region may be present. However, since the same target region as the target region of which the size is measured is included, a measurement result can be used. In addition, a plurality of first medical images (learning data) in which the target region is imaged from a plurality of distances and directions can be acquired for one target region, and the number of pieces of learning data can be easily increased.

An invention according to a ninth aspect is a medical image recognition apparatus comprising a second processor including a size recognizer, and a display or a speaker, in which the second processor acquires a second medical image from a modality, the size recognizer recognizes a size of a target region included in the second medical image in a case where the second medical image is input, and notifies, by the display or the speaker, the size of the target region recognized by the size recognizer, and the size recognizer is subjected to machine learning processing using the learning data created by the learning data creation apparatus according to any one of the first to eighth aspects of the present invention and recognizes the size of the target region included in the second medical image in a case where the second medical image is input.

According to the ninth aspect of the present invention, in a case where any second medical image is input, the size of the target region included in the second medical image can be automatically detected (recognized) by the size recognizer that is a learning model already subjected to machine learning using the learning data created by the learning data creation apparatus. A user can be notified of a recognition result (size of the target region). In this case, the second medical image input into a learner may not include the reference region. In addition, notification of the size of the target region to the user may be performed by displaying using the display or may be performed by voice from the speaker.

In the medical image recognition apparatus according to a tenth aspect of the present invention, it is preferable that the size recognizer is a neural network on which the machine learning processing is performed using the learning data.

In the medical image recognition apparatus according to an eleventh aspect of the present invention, it is preferable that the second processor includes a target region recognizer into which the second medical image is input and that recognizes the target region included in the second medical image, and the second processor notifies, by the display or the speaker, the size of the target region recognized by the size recognizer and positional information about the target region recognized by the target region recognizer. Accordingly, the user can check a position and the size of the target region included in the second medical image.

An invention according to a twelfth aspect is a learning data creation method for creating learning data for machine learning and sequentially storing the created learning data in a memory by a first processor, in which each processing of the first processor includes a step of acquiring a first medical image from a modality, a step of detecting a target region from the acquired first medical image, a step of detecting a reference region having a known size from the acquired first medical image, a step of determining whether or not the detected target region and the reference region are in contact, a step of measuring a size of the target region based on the size of the reference region in a case where a contact between the target region and the reference region is determined, and a step of storing, in the memory, as the learning data, a pair of the first medical image including the target region of which the size is measured, and the measured size of the target region.

In the learning data creation method according to a thirteenth aspect of the present invention, it is preferable that the reference region is a region in which an artificial object is imaged.

A learning data creation program according to a fourteenth aspect of the present invention causes a computer to implement a function of acquiring a first medical image from a modality, a function of detecting a target region from the acquired first medical image, a function of detecting a reference region having a known size from the acquired first medical image, a function of determining whether or not the detected target region and the reference region are in contact, a function of measuring a size of the target region based on the size of the reference region in a case where a contact between the target region and the reference region is determined, and a function of storing, in the memory, as learning data for machine learning, a pair of the first medical image including the target region of which the size is measured, and the measured size of the target region.

According to the present invention, the learning data for performing machine learning on the learning model recognizing the size of the target region included in the medical image can be efficiently created.

BRIEF DESCRIPTION OF THE DRAWINGS

FIG. 11 is a flowchart illustrating an embodiment of a learning data creation method according to the embodiment of the present invention.

DESCRIPTION OF THE PREFERRED EMBODIMENTS

Hereinafter, preferred embodiments of a learning data creation apparatus, a method, a program, and a medical image recognition apparatus according to the embodiment of the present invention will be described in accordance with the appended drawings.

Learning Data Creation Apparatus

Figure 1:
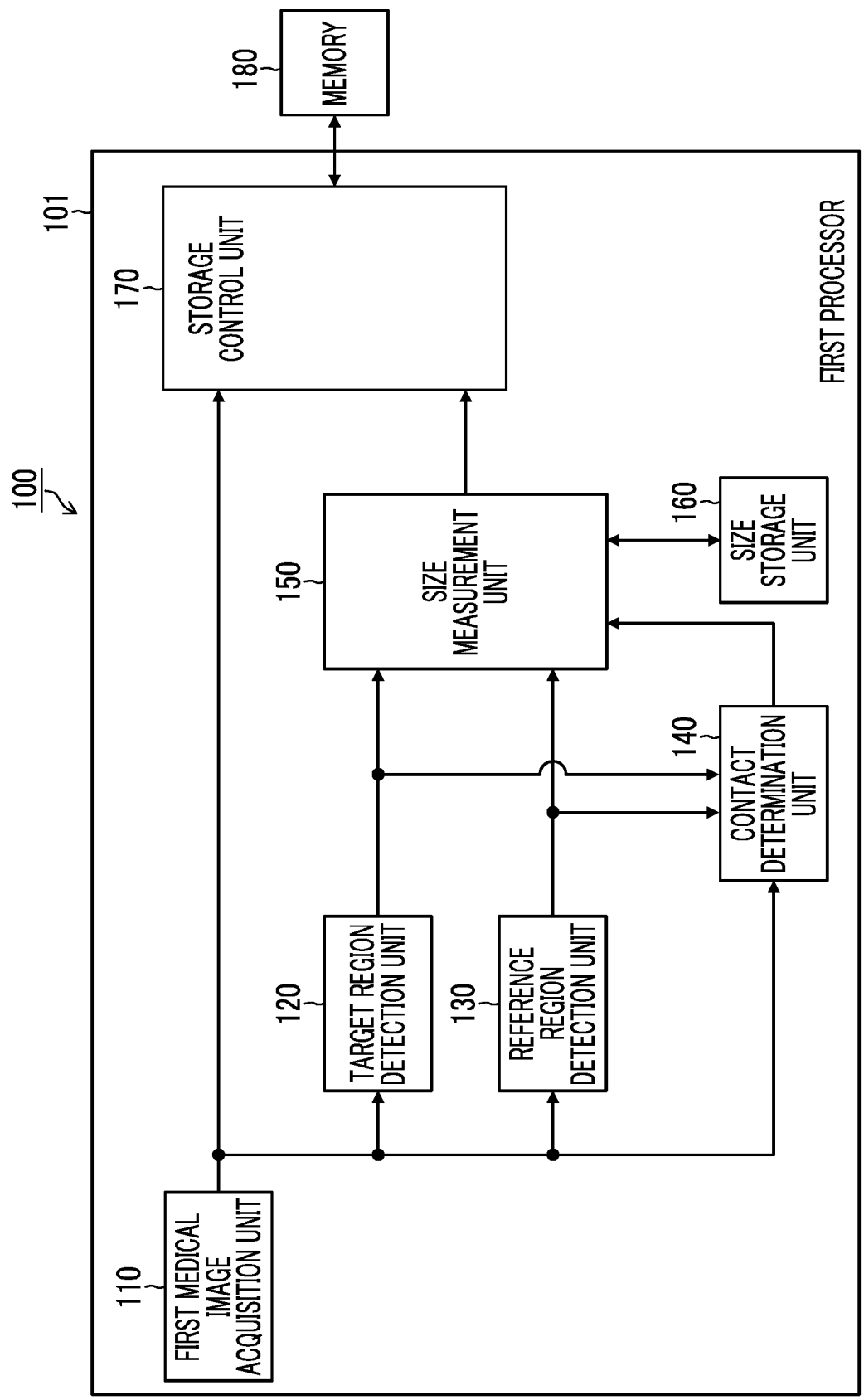
FIG. 1 is a block diagram illustrating a schematic configuration of a learning data creation apparatus 100 according to an embodiment of the present invention.

FIG. 1 is a block diagram illustrating a schematic configuration of the learning data creation apparatus according to the embodiment of the present invention.

A learning data creation apparatus 100 illustrated in FIG. 1 comprises a first processor 101 and a memory 180 storing learning data for machine learning.

The first processor 101 functions as a first medical image acquisition unit 110, a target region detection unit 120, a reference region detection unit 130, a contact determination unit 140, a size measurement unit 150, a size storage unit 160, and a storage control unit 170. For example, the learning data creation apparatus 100 can be configured with a computer. The computer can implement a function of each unit of the first processor 101 by installing a learning data creation program according to the embodiment of the present invention and executing the learning data creation program.

The first medical image acquisition unit 110 of the first processor 101 acquires a medical image (first medical image) from a modality such as an endoscope system, an ultrasonic diagnosis system, or an X-ray diagnosis system that captures the medical image. In the present example, the first medical image acquisition unit 110 acquires an endoscopic image captured by the endoscope system (an endoscope-scope and an endoscope processor) as the first medical image.

Figure 2:
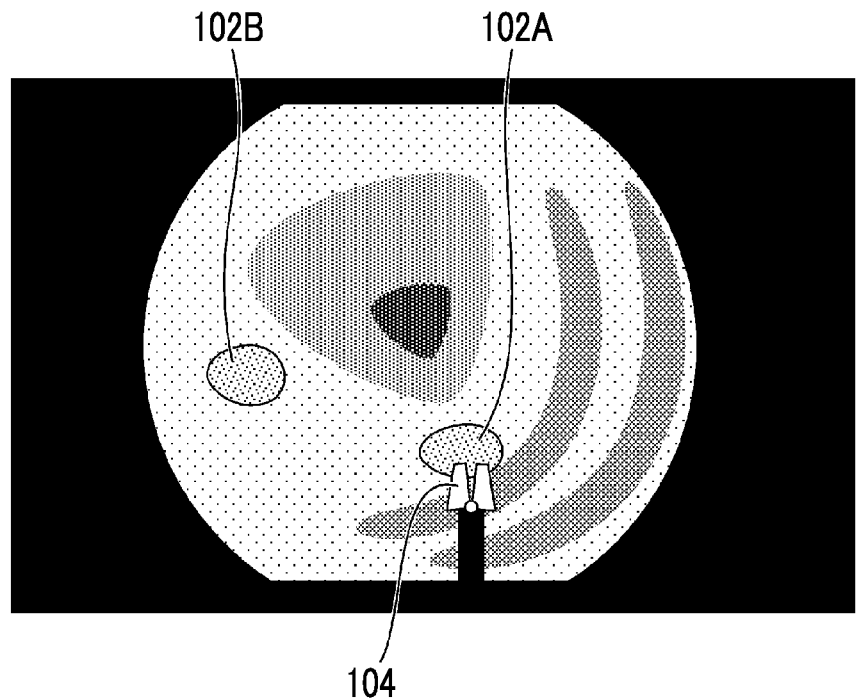
FIG. 2 is a diagram illustrating one example of a first medical image (endoscopic image) acquired by a first medical image acquisition unit 110 of the learning data creation apparatus 100.

FIG. 2 is a diagram illustrating one example of the first medical image (endoscopic image) acquired by the first medical image acquisition unit 110 illustrated in FIG. 1. The endoscopic image illustrated in FIG. 2 includes, described later, target regions 102A and 102B and a reference region 104.

The endoscopic image acquired by the first medical image acquisition unit 110 is output to the target region detection unit 120, the reference region detection unit 130, the contact determination unit 140, and the storage control unit 170.

The target region detection unit 120 is a part that detects the target region from the endoscopic image acquired by the first medical image acquisition unit 110, and outputs target region information (for example, positional information about each pixel in the target region) indicating the detected target region to the contact determination unit 140 and the size measurement unit 150.

For example, a recognizer that segments the target region using a convolutional neural network (CNN) can be used as the target region detection unit 120.

The target region is a region of which a size is desired to be measured, and is not limited to a lesion region and may be a normal region. In a case where the target region detection unit 120 detecting the target region is configured with the CNN, the target region detection unit 120 can be configured by learning and modeling a feature amount of the target region using a data set in which a pair of the target region and the endoscopic image including the target region is used as learning data.

Figure 3:
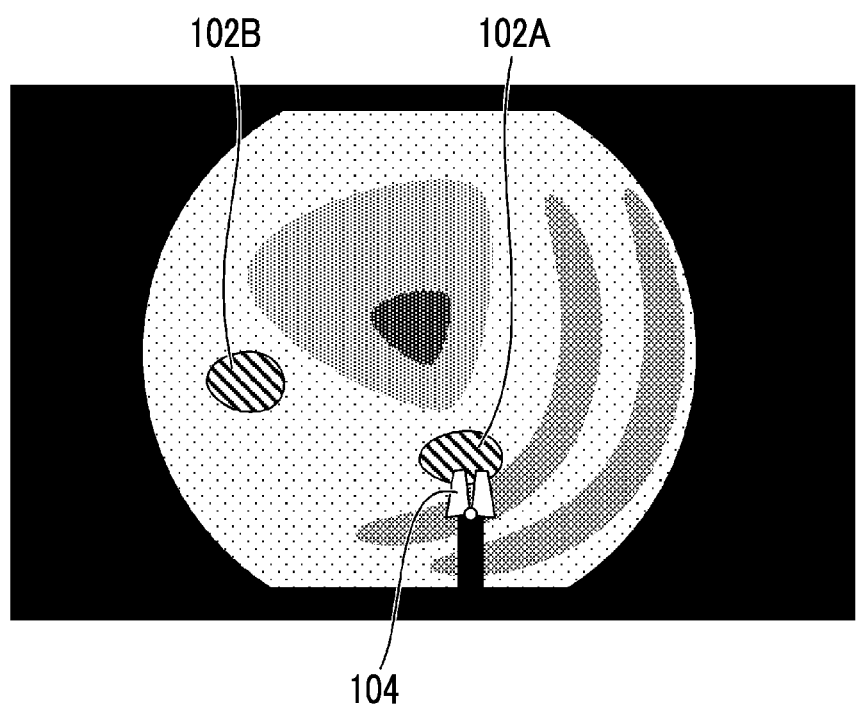
FIG. 3 is a diagram illustrating target regions 102A and 102B detected by a target region detection unit 120 of the learning data creation apparatus 100.

FIG. 3 is a diagram illustrating the target regions 102A and 102B (diagonal line portions) detected by the target region detection unit 120 illustrated in FIG. 1.

The reference region detection unit 130 is a part that detects the reference region from the endoscopic image acquired by the first medical image acquisition unit 110, and outputs reference region information (for example, positional information about each pixel in the reference region) indicating the detected reference region to the contact determination unit 140 and the size measurement unit 150.

In the same manner as the target region detection unit 120, a recognizer that segments the reference region using the CNN can be used as the reference region detection unit 130.

The reference region is preferably a region in which an artificial object having a known size is imaged, and the artificial object is preferably a treatment tool. Examples of the treatment tool include forceps such as biopsy forceps and measure forceps, a puncture needle, and a high-frequency knife, and in a case where the first medical image is an endoscopic image, a distal end hood and the like. The distal end hood is a transparent cylindrical hood attached to a distal end of the endoscope-scope and is used for securing an endoscopic field of view in a case of performing imaging near an observed part and securing an imaging distance to the observed part.

The reference region detection unit 130 preferably detects the reference region and detects a type of artificial object (treatment tool) captured in the reference region. The type of treatment tool can be detected using the CNN on which machine learning is performed in order to classify the treatment tool.

Figure 4:
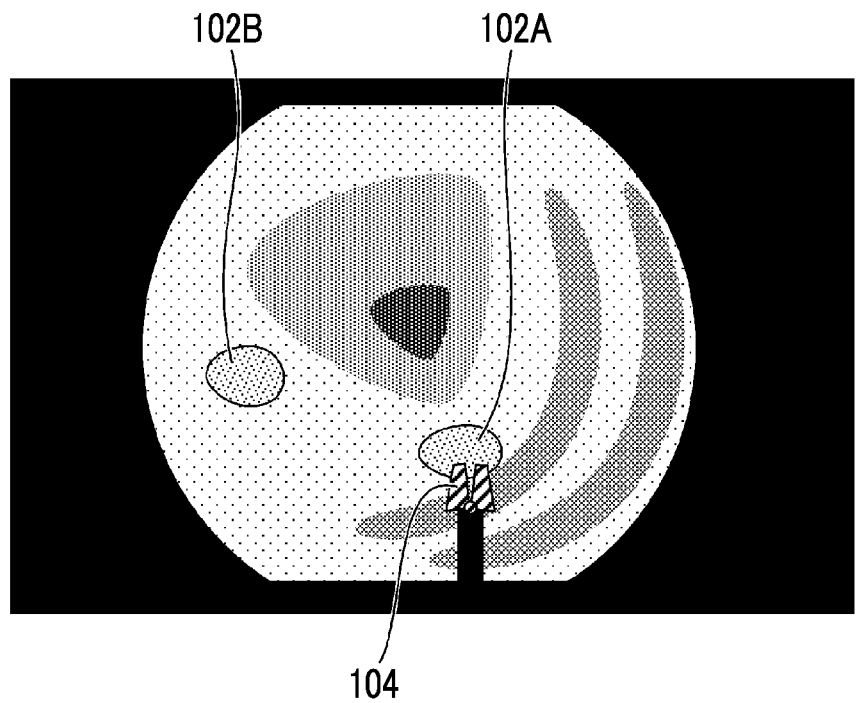
FIG. 4 is a diagram illustrating a reference region 104 detected by a reference region detection unit 130 of the learning data creation apparatus 100.

FIG. 4 is a diagram illustrating the reference region 104 (diagonal line portion) detected by the reference region detection unit 130 illustrated in FIG. 1.

The contact determination unit 140 is a determination unit that determines whether or not the target region and the reference region detected from the same endoscopic image are in contact, and outputs a determination result of contact to the size measurement unit 150. In a case where a plurality of target regions are detected from the same endoscopic image, the contact determination unit 140 also determines whether or not the reference region is in contact with any target region.

The contact determination unit 140 includes a contact detection unit that detects whether or not the artificial object is in contact with the target region or a region in a vicinity of the target region, and determines whether or not the target region and the reference region are in contact based on a detection result of the contact detection unit. The "contact" detected by the contact detection unit includes not only a case where the artificial object indicated by the reference region is physically in contact with a surface of a subject indicated by the target region, but also a case where the surface of the subject and the artificial object are very close to each other and a distance therebetween is regarded as zero.

The contact determination unit 140 of the present example determines whether or not the target region and the reference region are in contact, by image processing using the first medical image (endoscopic image) input from the first medical image acquisition unit 110, the target region information indicating the target region detected from the same endoscopic image, and the reference region information indicating the reference region.

In a case where the reference region overlaps with the target region on the endoscopic image, the contact determination unit 140 determines whether or not the reference region is present in the region in the vicinity of the target region. In a case where the size of the target region is measured based on a size of the reference region as described later, the vicinity of the target region refers to being within a distance from the target region in a case where a measurement error is within an allowable range.

In a case where the contact determination unit 140 determines, in a case where the reference region overlaps with the target region, that the reference region is present in the region in the vicinity of the target region, an image processing unit that functions as the contact detection unit detects a contact between the target region and the artificial object based on image feature amounts of the target region and the reference region. For example, since a contact part is distorted in a case where the artificial object comes into contact with the target region, the contact between the target region and the artificial object can be detected by detecting an image feature amount of the contact part by image processing or detecting the image feature amount using a recognizer such as the CNN on which machine learning is performed.

The contact detection unit may be configured with a contact sensor that is arranged at a distal end of the artificial object and detects the contact between the target region and the artificial object. In this case, whether or not the artificial object is in contact with the surface of the subject can be detected using a detection signal of the contact sensor.

In a case of a stereo endoscope using a stereo camera, a distance to the surface of the subject indicated by the target region and a distance to the distal end of the artificial object indicated by the reference region from the distal end of the endoscope can be measured. In a case where these distances almost match, it can be determined (detected) that the artificial object is in contact with the surface of the subject.

Figure 5:
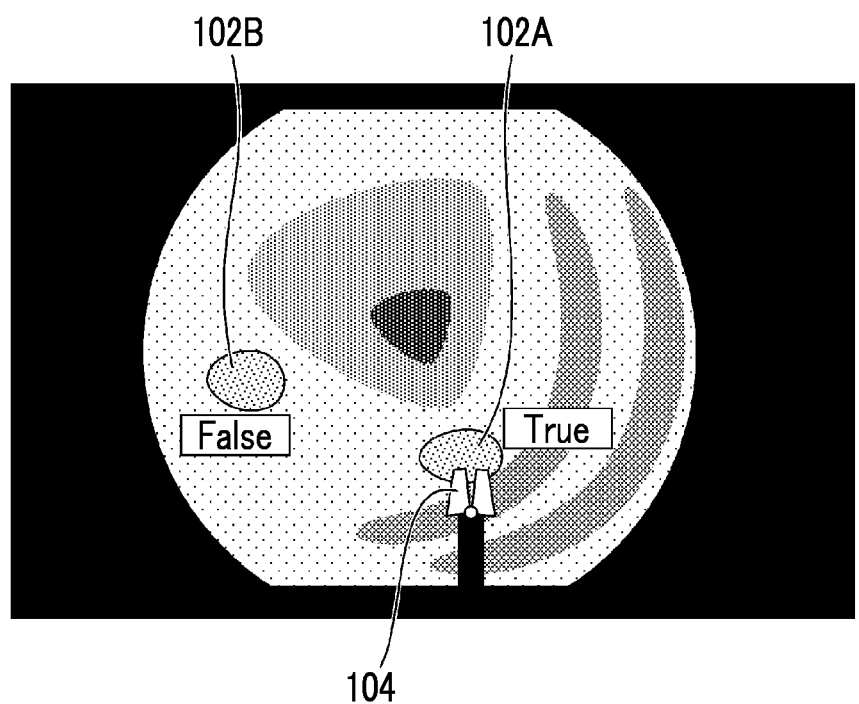
FIG. 5 is a diagram illustrating a determination result in which a contact determination unit 140 of the learning data creation apparatus 100 determines a contact between a target region and a reference region.

FIG. 5 is a diagram illustrating a determination result in which a contact between the target region and the reference region is determined by the contact determination unit 140.

In the example illustrated in FIG. 5, a determination result of contact in a case where the target region 102A out of two target regions 102A and 102B and the reference region 104 are in contact is illustrated.

In a case where the contact determination unit 140 determines the contact between the target region 102A and the reference region 104, the size measurement unit 150 acquires the target region information indicating the target region 102A from the target region detection unit 120, and acquires the reference region information indicating the reference region 104 from the reference region detection unit 130.

In addition, the size measurement unit 150 acquires a size (actual size) of the artificial object captured in the reference region 104 from the size storage unit 160. In a case where the reference region detection unit 130 detects the type of artificial object captured in the detected reference region, the size measurement unit 150 acquires information indicating the type of artificial object from the reference region detection unit 130 and reads out a size corresponding to the type of artificial object from the size storage unit 160.

In a case where the user knows the artificial object such as the forceps to be used in advance before an endoscopic test is started, the user may input information indicating the artificial object to be used using an operation unit such as a keyboard, or may directly input the size of the artificial object. The size of the artificial object is preferably a size of the distal end of the artificial object.

The artificial object captured in the reference region 104 illustrated in FIG. 2 and the like is biopsy forceps. In a case of biopsy forceps, the biopsy forceps are pushed against a portion subjected to biopsy in a state where distal end claw portions of the biopsy forceps is open. Then, a tissue slice is cut out by closing the distal end claw portions. Thus, an exterior width of the distal end claw portions in a state where the distal end claw portions are open can be used as a known size of the biopsy forceps. Alternatively, a size of a part that does not depend on opening and closing of the distal end claw portions of the biopsy forceps can be used as the known size of the biopsy forceps.

The size measurement unit 150 calculates an actual size per pixel of the endoscopic image in the reference region 104 and a vicinity of the reference region 104 based on the reference region information indicating the reference region 104 and the actual size of the artificial object captured in the reference region 104. In addition, the size measurement unit 150 calculates a major axis of an ellipse circumscribing the target region 102A on the endoscopic image based on the target region information (for example, the positional information about each pixel in the target region) about the target region 102A.

The size measurement unit 150 calculates an actual size of the major axis of the ellipse circumscribing the target region 102A based on the calculated actual size per pixel of the endoscopic image and the major axis of the ellipse circumscribing the target region 102A on the endoscopic image, and outputs the calculated actual size to the storage control unit 170 as a size of the target region 102A.

The size measurement unit 150 is not limited to a case of measuring the size of the major axis of the ellipse circumscribing the target region and may measure sizes of the major axis and a minor axis of the ellipse circumscribing the target region or measure a size of a diameter of a circle circumscribing the target region.

The storage control unit 170 stores, in the memory 180, as learning data of a learning model, a pair of the endoscopic image that is the first medical image (endoscopic image) input from the first medical image acquisition unit and is used for calculating the size of the target region 102A, and the size (measurement result) of the target region 102A measured by the size measurement unit 150. That is, the storage control unit 170 stores the first medical image (endoscopic image) constituting the pair as input data of the learning model and stores the size of the target region as answer data of the learning model in the memory 180.

The memory 180 is a memory such as a hard disk apparatus or a flash memory and is preferably a non-volatile memory storing a storage content even in a case where power is not supplied.

Figure 6A:
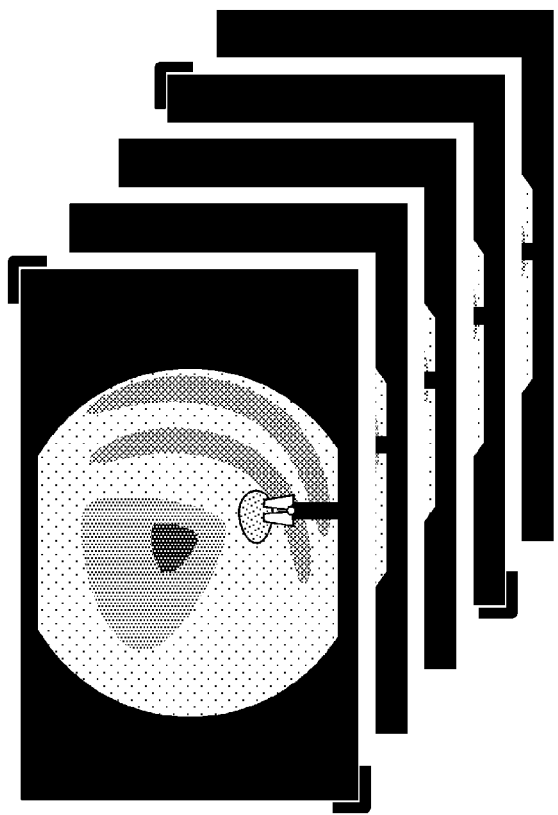
FIG. 6A is a diagram illustrating a first medical image group acquired by the first medical image acquisition unit 110.
Figure 6B:
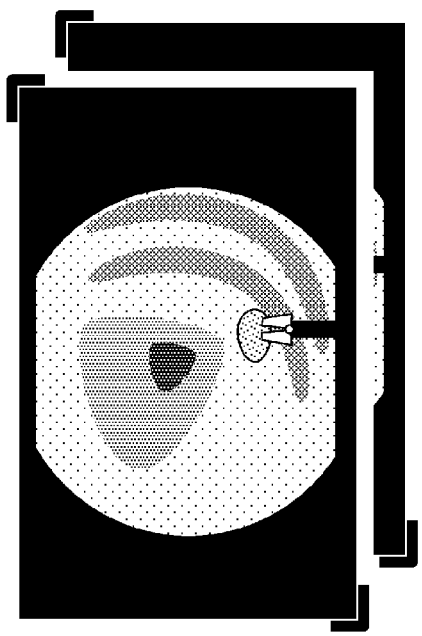
FIG. 6B is a diagram illustrating a learning image group that is extracted from the first medical image group and in which the target region and the reference region are in contact.

FIG. 6A is a diagram illustrating a first medical image group acquired by the first medical image acquisition unit 110, and FIG. 6B is a diagram illustrating a learning image group that is extracted from the first medical image group and in which the target region and the reference region are in contact. The size of the target region in each first medical image is associated with each first medical image of the learning image group as the answer data.

According to the learning data creation apparatus 100 having the above configuration, a large number of data sets of the learning data necessary for performing machine learning on the learning model recognizing the size of the target region included in the first medical image can be efficiently created.

Figures 7A, 7B:
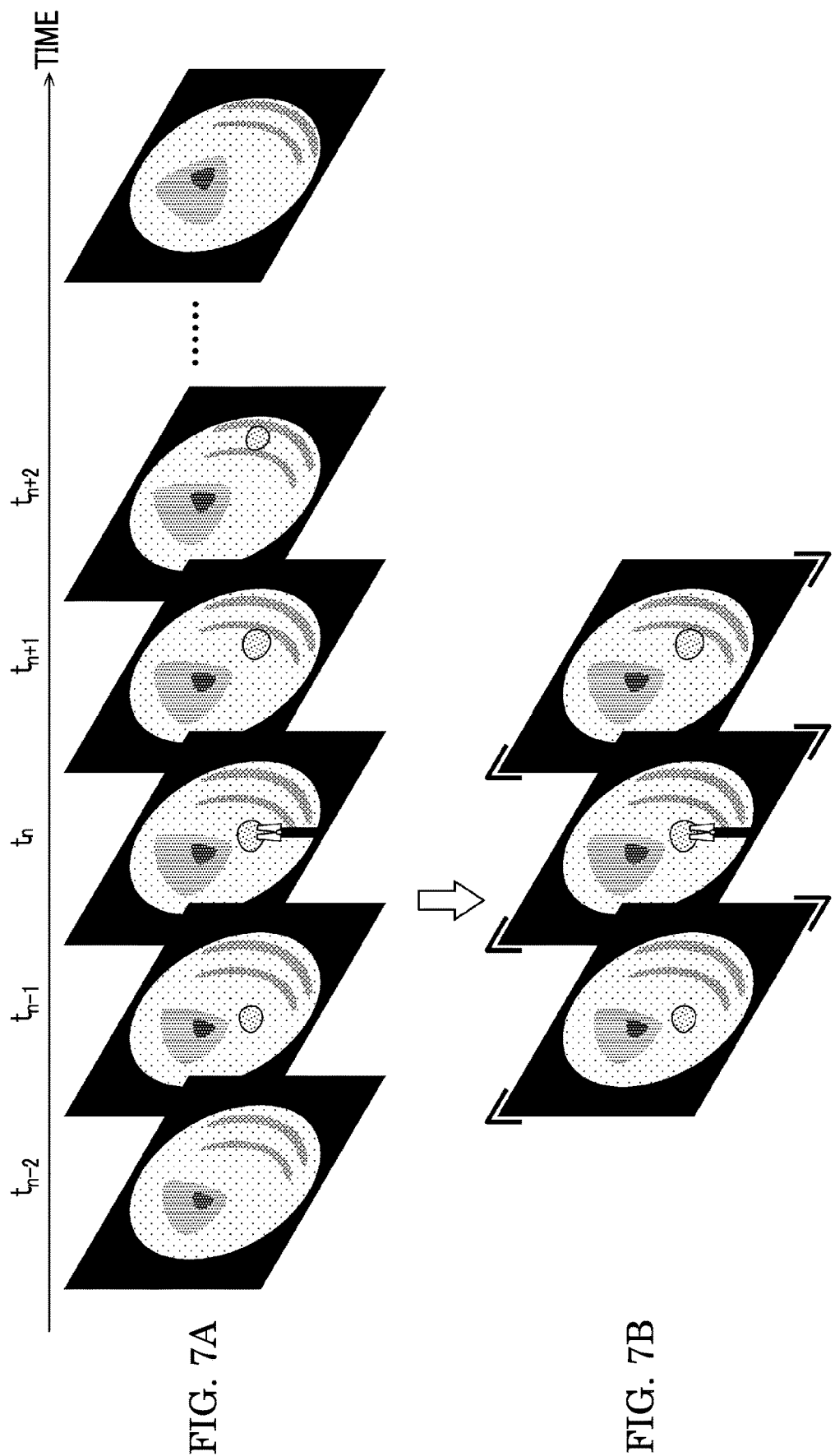
FIG. 7A is a diagram illustrating a time series of first medical images (endoscopic images) acquired by the first medical image acquisition unit 110.
FIG. 7B is a diagram illustrating an embodiment of learning images extracted from the time series of endoscopic images.

FIG. 7A is a diagram illustrating a time series of first medical images (endoscopic images) acquired by the first medical image acquisition unit 110, and FIG. 7B is a diagram illustrating an embodiment of learning images extracted from the time series of endoscopic images.

In the embodiment illustrated in FIGS. 7A and 7B, an endoscopic image of time $t_n$ is an image in which the target region and the reference region are in contact. Endoscopic images of time $t_{n-1}$ and time $t_{n+1}$ before and after time $t_n$ are images in which the target region and the reference region are not in contact.

However, the endoscopic images of time $t_{n-1}$ and time $t_{n+1}$ are images of which an imaging time is close to the endoscopic image of time $t_n$, and are images having a high possibility of including the same target region as the target region in the endoscopic image of time $t_n$.

Therefore, in addition to the endoscopic image of time $t_n$ in which the target region and the reference region are in contact, the storage control unit 170 stores, in the memory 180, as the learning image, an endoscopic image that is captured before or after the endoscopic image of time $t_n$ and includes the same target region as the target region in the endoscopic image of time $t_n$.

In the example illustrated in FIG. 7B, the endoscopic image of time $t_n$ in which the target region and the reference region are in contact, and the endoscopic images of time $t_{n-1}$ and time $t_{n+1}$ captured before and after the endoscopic image of time $t_n$ are extracted as the learning images from the time series of endoscopic images illustrated in FIG. 7A. The size of the target region in the endoscopic image of time $t_n$ is set as answer data paired with each of the endoscopic images of time $t_{n-1}$ and time $t_{n+1}$.

Accordingly, the learning data can be more efficiently collected. In addition, in a case of the endoscopic image that is before or after the endoscopic image in which the target region and the reference region are in contact, and that includes the same target region as the target region in the endoscopic image in which the target region and the reference region are in contact, the endoscopic image may not include the reference region.

Medical Image Recognition Apparatus

Figure 8:
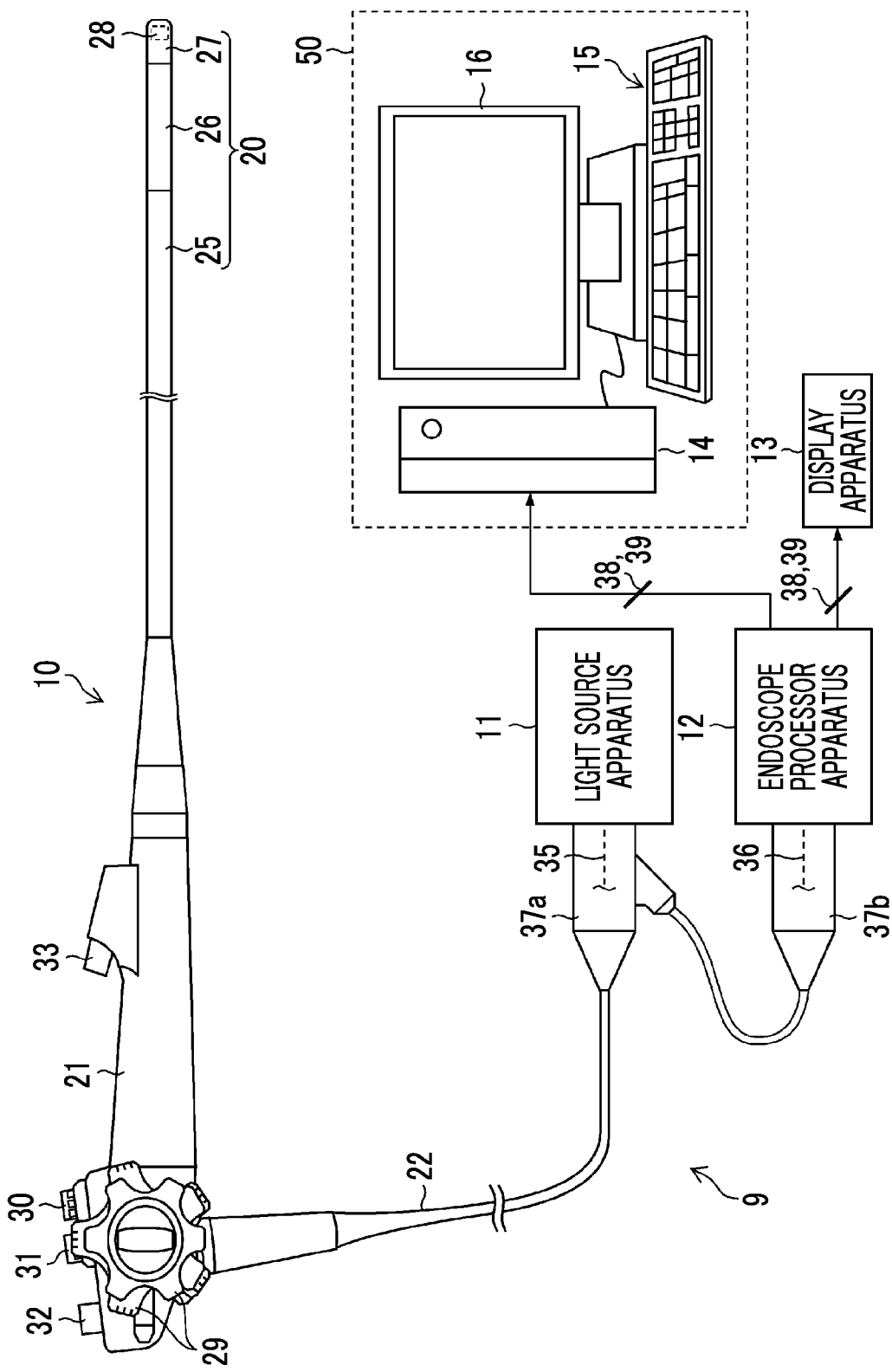
FIG. 8 is a schematic diagram illustrating an overall configuration of an endoscope system 9 including a medical image recognition apparatus 50 according to the embodiment of the present invention.

FIG. 8 is a schematic diagram illustrating an overall configuration of an endoscope system 9 including a medical image recognition apparatus 50 according to the embodiment of the present invention.

As illustrated in FIG. 8, the endoscope system 9 comprises an endoscope-scope 10 that is an electronic endoscope, a light source apparatus 11, an endoscope processor apparatus 12, a display apparatus 13, and the medical image recognition apparatus 50. The medical image recognition apparatus 50 comprises a second processor 14, an operation unit 15, and a display 16.

The endoscope-scope 10 images a time series of medical images (second medical images) including a subject image and is, for example, a flexible endoscope. The endoscope-scope 10 includes an insertion part 20 that is inserted into a test object and has a distal end and a proximal end, a hand operation unit 21 that is consecutively installed on a proximal end side of the insertion part 20 and is held by the user for performing various operations, and a universal cord 22 that is consecutively installed with the hand operation unit 21.

The entire insertion part 20 is formed in a long shape having a small diameter. The insertion part 20 is configured by consecutively installing, in order from the proximal end side toward a distal end side, a flexible portion 25 that has flexibility, a bending portion 26 that can be bent by operating the hand operation unit 21, and a distal end portion 27 that incorporates an imaging optical system (objective lens), not illustrated, an imaging element 28, and the like.

The imaging element 28 is an imaging element of a complementary metal oxide semiconductor (CMOS) type or a charge coupled device (CCD) type. Image light of the observed part is incident on an imaging surface of the imaging element 28 through an observation window, not illustrated, that is open on a distal end surface of the distal end portion 27, and an objective lens, not illustrated, that is arranged behind the observation window. The imaging element 28 outputs an image signal by imaging (converting into an electric signal) the observed part incident on the imaging surface.

Various operation members operated by the user are disposed in the hand operation unit 21. Specifically, two types of bending operation knobs 29 that are used for a bending operation for the bending portion 26, an air supply and water supply button 30 for an air supply and water supply operation, and a suction button 31 for a suction operation are disposed in the hand operation unit 21. In addition, a still picture imaging instruction unit 32 for providing an imaging instruction for a still picture 39 of the observed part and a treatment tool introduction port 33 through which the treatment tool (not illustrated) is inserted into a treatment tool insertion path (not illustrated) passing through the insertion part 20 are disposed in the hand operation unit 21.

The universal cord 22 is a connection cord for connecting the endoscope-scope 10 to the light source apparatus 11. The universal cord 22 includes a light guide 35 that passes through the insertion part 20, a signal cable 36, and a fluid tube (not illustrated). In addition, a connector 37a that is connected to the light source apparatus 11, and a connector 37b that branches from the connector 37a and is connected to the endoscope processor apparatus 12 are disposed in an end portion of the universal cord 22.

The light guide 35 and the fluid tube (not illustrated) are inserted into the light source apparatus 11 by connecting the connector 37a to the light source apparatus 11. Accordingly, necessary illumination light, water, and air are supplied to the endoscope-scope 10 from the light source apparatus 11 through the light guide 35 and the fluid tube (not illustrated). Consequently, the observed part is irradiated with the illumination light from the illumination window (not illustrated) on the distal end surface of the distal end portion 27. In addition, in accordance with a push operation performed on the air supply and water supply button 30, air or water is ejected toward the observation window (not illustrated) on the distal end surface from an air supply and water supply nozzle (not illustrated) on the distal end surface of the distal end portion 27.

The signal cable 36 and the endoscope processor apparatus 12 are electrically connected by connecting the connector 37b to the endoscope processor apparatus 12. Accordingly, through the signal cable 36, an image signal of the observed part is output to the endoscope processor apparatus 12 from the imaging element 28 of the endoscope-scope 10, and a control signal is output to the endoscope-scope 10 from the endoscope processor apparatus 12.

The light source apparatus 11 supplies the illumination light to the light guide 35 of the endoscope-scope 10 through the connector 37a. Light of various wavelength ranges corresponding to an observation purpose such as white light (light of a white wavelength range or light of a plurality of wavelength ranges), light of a specific one or plurality of wavelength ranges, or a combination thereof is selected as the illumination light. The specific wavelength range is a range narrower than the white wavelength range.

For example, a first example of the specific wavelength range is a blue range or a green range of a visible range. The wavelength range of the first example includes a wavelength range of greater than or equal to 390 nm and less than or equal to 450 nm or greater than or equal to 530 nm and less than or equal to 550 nm. Light of the first example has a peak wavelength in the wavelength range of greater than or equal to 390 nm and less than or equal to 450 nm or greater than or equal to 530 nm and less than or equal to 550 nm.

For example, a second example of the specific wavelength range is a red range of the visible range. The wavelength range of the second example includes a wavelength range of greater than or equal to 585 nm and less than or equal to 615 nm or greater than or equal to 610 nm and less than or equal to 730 nm. Light of the second example has a peak wavelength in the wavelength range of greater than or equal to 585 nm and less than or equal to 615 nm or greater than or equal to 610 nm and less than or equal to 730 nm.

A third example of the specific wavelength range includes a wavelength range of which a light absorption coefficient varies between oxyhemoglobin and reduced hemoglobin. Light of the third example has a peak wavelength in the wavelength range of which the light absorption coefficient varies between the oxyhemoglobin and the reduced hemoglobin. The wavelength range of the third example includes a wavelength range of 400±10 nm, 440±10 nm, 470±10 nm, or greater than or equal to 600 nm and less than or equal to 750 nm. Light of the third example has a peak wavelength in the wavelength range of 400±10 nm, 440±10 nm, 470±10 nm, or greater than or equal to 600 nm and less than or equal to 750 nm.

A fourth example of the specific wavelength range is a wavelength range (390 nm to 470 nm) of excitation light that is used for observing (fluorescence observation) fluorescence emitted by a fluorescent substance in a living body and excites the fluorescent substance.

A fifth example of the specific wavelength range is a wavelength range of infrared light. The wavelength range of the fifth example includes a wavelength range of greater than or equal to 790 nm and less than or equal to 820 nm or greater than or equal to 905 nm and less than or equal to 970 nm. Light of the fifth example has a peak wavelength in the wavelength range of greater than or equal to 790 nm and less than or equal to 820 nm or greater than or equal to 905 nm and less than or equal to 970 nm.

The endoscope processor apparatus 12 controls an operation of the endoscope-scope 10 through the connector 37b and the signal cable 36. In addition, the endoscope processor apparatus 12 generates an image (referred to as a "motion picture 38") consisting of a time series of frame images 38a including the subject image based on the image signal acquired from the imaging element 28 of the endoscope-scope 10 through the connector 37b and the signal cable 36. Furthermore, in a case where the still picture imaging instruction unit 32 is operated in the hand operation unit 21 of the endoscope-scope 10, the endoscope processor apparatus 12 sets one frame image of the motion picture 38 as the still picture 39 corresponding to a timing of the imaging instruction in parallel with generation of the motion picture 38.

The motion picture 38 and the still picture 39 are medical images obtained by imaging an inside of the test object, that is, the living body. Furthermore, in a case where the motion picture 38 and the still picture 39 are images obtained by the light (special light) of the specific wavelength range, both images are special light images. The endoscope processor apparatus 12 outputs the generated motion picture 38 and the still picture 39 to each of the display apparatus 13 and the medical image recognition apparatus 50.

The endoscope processor apparatus 12 may generate (acquire) the special light image having information about the specific wavelength range based on a normal light image obtained by the white light. In this case, the endoscope processor apparatus 12 functions as a special light image acquisition unit. The endoscope processor apparatus 12 obtains a signal of the specific wavelength range by performing calculation based on color information about red, green, and blue (RGB) or cyan, magenta, and yellow (CMY) included in the normal light image.

In addition, for example, the endoscope processor apparatus 12 may generate a feature amount image such as a well-known oxygen saturation image based on at least one of the normal light image obtained by the white light or the special light image obtained by the light (special light) of the specific wavelength range. In this case, the endoscope processor apparatus 12 functions as a feature amount image generation unit. Any of the motion picture 38 or the still picture 39 including the image of the inside of the living body, the normal light image, the special light image, and the feature amount image is a medical image obtained by imaging a result of imaging or measuring a body of a person for diagnosis and testing purposes based on images.

The display apparatus 13 is connected to the endoscope processor apparatus 12 and functions as a display that displays the motion picture 38 and the still picture 39 input from the endoscope processor apparatus 12. The user (doctor) performs an advancing and receding operation or the like on the insertion part 20 while checking the motion picture 38 displayed on the display apparatus 13. In a case where a lesion or the like is found in the observed part, the user executes imaging of a still picture of the observed part by operating the still picture imaging instruction unit 32 and performs a diagnosis, a biopsy, resection of the lesion region, and the like.

Medical Image Recognition Apparatus

The medical image recognition apparatus 50 detects, based on the time series of medical images, the size of the target region such as the lesion included in the medical image being captured and notifies the user of the detected size by the display 16 or the like. In the present embodiment, for example, a computer is used as the medical image recognition apparatus 50. In addition, a keyboard, a mouse, and the like connected to the computer in a wired or wireless manner are used as the operation unit 15. Various monitors such as a liquid crystal monitor connectable to the computer are used as the display 16 functioning as a notification unit.

Embodiment of Medical Image Recognition Apparatus 50

Figure 9:
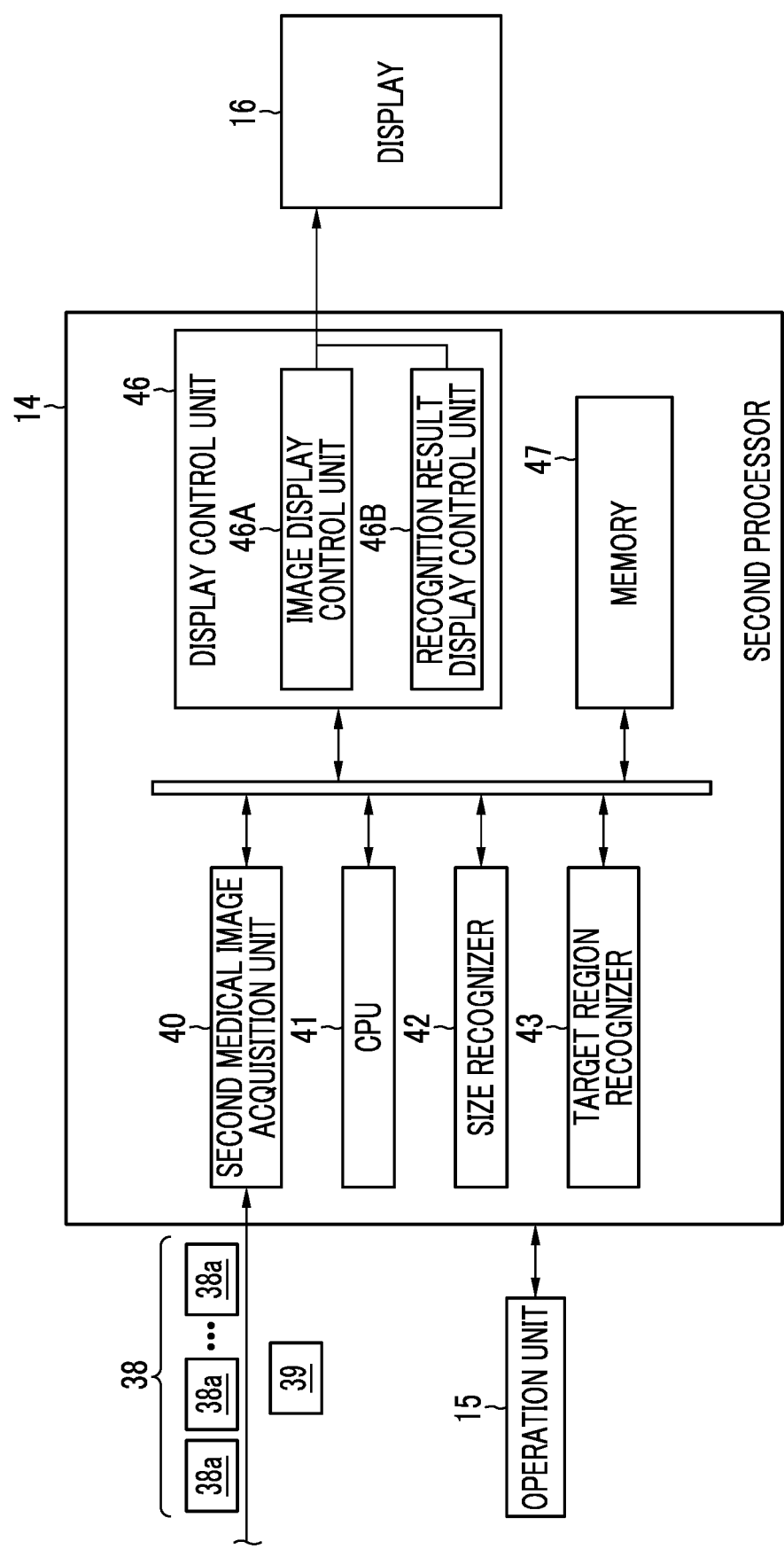
FIG. 9 is a block diagram illustrating an embodiment of the medical image recognition apparatus 50 illustrated in FIG. 8.

FIG. 9 is a block diagram illustrating an embodiment of the medical image recognition apparatus 50 illustrated in FIG. 8.

In FIG. 9, the medical image recognition apparatus 50 comprises the second processor 14 and the display 16.

The second processor 14 includes a second medical image acquisition unit 40, a central processing unit (CPU) 41, a size recognizer 42, a target region recognizer 43, a display control unit 46, and a memory 47.

The CPU 41 operates based on a program stored in the memory 47, manages and controls the second medical image acquisition unit 40, the size recognizer 42, the target region recognizer 43, and the display control unit 46, and functions as a part of each unit of the second medical image acquisition unit 40, the size recognizer 42, the target region recognizer 43, and the display control unit 46.

The second medical image acquisition unit 40 acquires, from the endoscope processor apparatus 12, the second medical image (in the present example, the motion picture 38 imaged by the endoscope-scope 10) consisting of a time series of frame images 38a including the subject image using an image input and output interface, not illustrated, that is connected to the endoscope processor apparatus 12 (FIG. 8) in a wired or wireless manner.

The size recognizer 42 is a learning model on which machine learning processing is performed using the learning data created by the learning data creation apparatus 100 illustrated in FIG. 1, and is a part that infers (recognizes) the size of the target region such as the lesion included in the input frame image 38a in a case where each frame image 38a of the motion picture 38 acquired by the second medical image acquisition unit 40 is input.

For example, the size recognizer 42 can be configured with the CNN which is one type of neural network. A parameter of a filter used in a plurality of convolutional layers of intermediate layers of the CNN, a weight coefficient of a fully connected layer, and the like are updated and optimized in order to infer the size of the target region using multiple data sets of the learning data created by the learning data creation apparatus 100. The size recognizer 42 is not limited to a function of updating the parameter and the like using the learning data created by the learning data creation apparatus 100. The parameter and the like of another learning model optimized using the parameter and the like using the learning data created by the learning data creation apparatus 100 may be applied to the size recognizer 42.

The target region recognizer 43 can be configured in the same manner as the target region detection unit 120 illustrated in FIG. 1. In a case where the frame image 38a is input, the target region recognizer 43 recognizes (detects) the target region such as the lesion included in the frame image 38a and outputs positional information indicating a position of the target region in the frame image 38a. In this case, for example, positional information about two points at diagonal corners of a rectangular frame in a case where the target region in the frame image is surrounded by the rectangular frame is considered as positional information about the target region.

The target region recognizer 43 may further have a classification function of classifying the target region included in the frame image 38a into any one of two or more classes based on the frame image 38a. For example, as two or more classes, it is considered that classification into one class of three classes of "neoplastic", "non-neoplastic", and "others" is performed. However, classes of classification are not limited thereto. For example, classification based on a shape, a position, and the like of a tumor, classification based on severity of the target region, and classification of a combination thereof can be included.

While the size recognizer 42 recognizes and outputs the size of the target region based on the input frame image 38a, the size recognizer 42 may further output the positional information about the target region.

The display control unit 46 includes an image display control unit 46A that generates and outputs image data for display to the display 16 based on the second medical image (the motion picture 38 and the still picture 39) acquired by the second medical image acquisition unit 40, and a recognition result display control unit 46B that generates and outputs, to the display 16, image data for display indicating the size (recognition result), recognized by the size recognizer 42, of the target region included in the second medical image and the position (recognition result) of the target region recognized by the target region recognizer 43.

The display control unit 46 displays a medical image and the recognition result of the target region on the display 16 by compositing the image data output from the image display control unit 46A with the image data indicating the recognition result (the size and the position) of the target region output from the recognition result display control unit 46B and outputting composited composite image data to the display 16. Accordingly, the size of the target region recognized by the size recognizer 42 and the position of the target region recognized by the target region recognizer 43 are notified.

Figure 10:
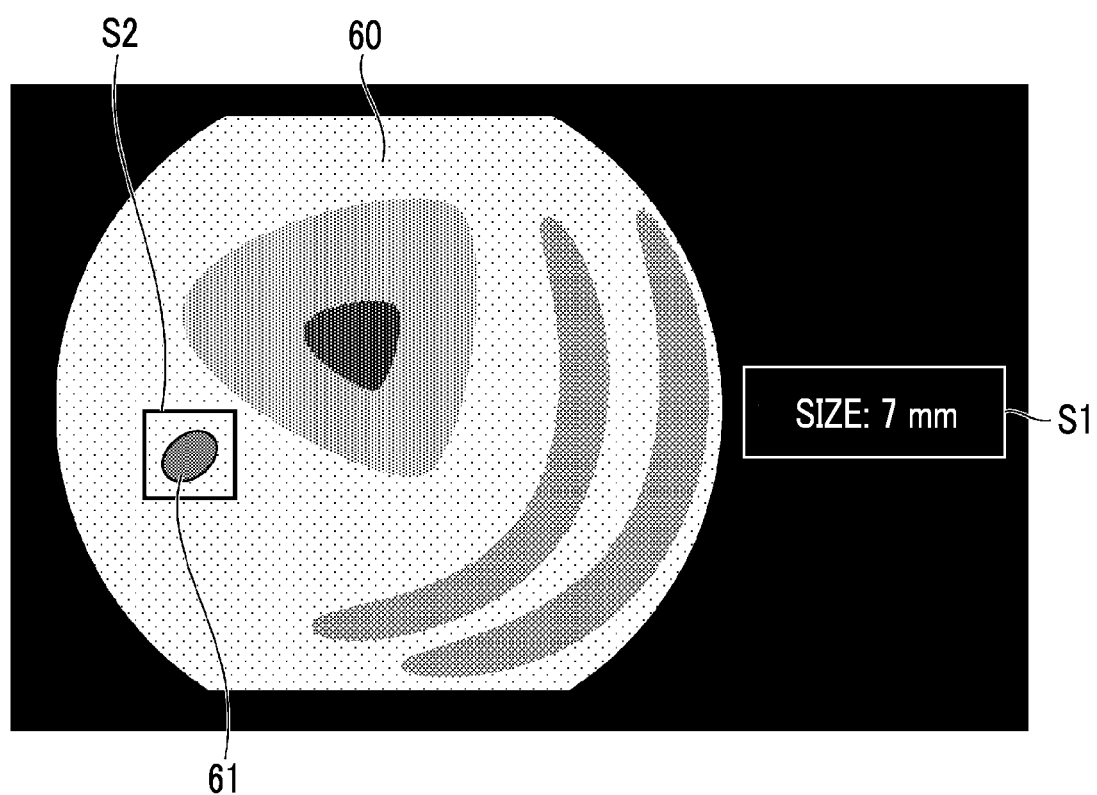
FIG. 10 is a diagram illustrating one example of a recognition result of a medical image and the target region displayed on a display 16.

FIG. 10 is a diagram illustrating one example of the medical image and the recognition result displayed on the display 16.

In FIG. 10, a target region included in a medical image 60 is denoted by 61. Size information indicating a size of the target region 61 is denoted by S1. Positional information (in the present example, a rectangular frame) indicating a position of the target region 61 is denoted by S2.

The recognition result display control unit 46B can generate image data indicating the rectangular frame S2, output the image data to the display 16, and display the rectangular frame S2 on the display 16 based on the positional information about two points at the diagonal corners of the rectangular frame in a case where the target region is surrounded by the rectangular frame.

The user can check the size (in the present example, 7 mm) of the target region 61 by the size information S1 displayed in a display region adjacent to the medical image 60 and can check the position of the target region 61 in the medical image 60 by the rectangular frame S2 displayed in a superimposed manner on the medical image 60. The size information S1 may be displayed in a superimposed manner at a position adjacent to the rectangular frame S2 on the medical image 60. The size of the target region 61 is not limited to a case of text notification by the display 16 and may be notified by voice using a speaker, not illustrated, or may be notified by text and voice.

The memory 47 includes a storage region as a work region of the CPU 41 and a storage region storing various programs such as an operating system and a medical image recognition processing program, the imaged still picture 39, and the like.

The medical image recognition apparatus 50 may include the entirety or a part of the learning data creation apparatus 100 illustrated in FIG. 1.

For example, in a case where the reference region such as the artificial object is present in the second medical image acquired by the second medical image acquisition unit 40 and the reference region is in contact with the target region, the size of the target region is measured by the size measurement unit 150 by acquiring the second medical image as the first medical image. The measured size of the target region may be displayed on the display 16 instead of the size recognized by the size recognizer 42. In addition, a pair of the second medical image acquired as the first medical image by the second medical image acquisition unit 40 and the size of the target region measured by the size measurement unit 150 may be recorded in the memory 47.

Learning Data Creation Method

FIG. 11 is a flowchart illustrating an embodiment of a learning data creation method according to the embodiment of the present invention and illustrates a processing procedure of each unit of the learning data creation apparatus 100 illustrated in FIG. 1.

In FIG. 11, the first medical image acquisition unit 110 of the first processor 101 acquires the endoscopic image (first medical image) of one frame in the time series of endoscopic images from the modality (in the present example, the endoscope system) capturing the medical image (step S10).

The target region detection unit 120 detects the target region from the endoscopic image acquired by the first medical image acquisition unit 110 (step S12).

In a case where the target region is detected by the target region detection unit 120 (in a case of "Yes" in step S14), a transition is made to step S16. In a case where the target region is not detected (in a case of "No" in step S14), a return is made to step S10 in order to acquire a subsequent frame.

In step S16, the reference region detection unit 130 detects the reference region from the endoscopic image acquired by the first medical image acquisition unit 110.

In a case where the reference region is detected by the reference region detection unit 130 (in a case of "Yes" in step S18), a transition is made to step S20. In a case where the reference region is not detected (in a case of "No" in step S18), a return is made to step S10 in order to acquire the subsequent frame.

In step S20, the contact determination unit 140 determines whether or not the target region detected in step S12 and the reference region detected in step S16 are in contact.

In a case where a contact is detected by the contact determination unit 140 (in a case of "Yes" in step S22), a transition is made to step S24. In a case where a contact is not detected (in a case of "No" in step S22), a return is made to step S10 in order to acquire the subsequent frame.

In step S24, the size measurement unit 150 calculates the actual size per pixel of the endoscopic image in the reference region and the vicinity of the reference region based on the known size (actual size) of the artificial object captured in the reference region 104 and the reference region information indicating the reference region 104, and measures, as the size of the target region, the actual size of the major axis of the ellipse circumscribing the target region based on the calculated actual size per pixel and the target region information about the target region.

Next, the storage control unit 170 stores, in the memory 180, the learning data of the pair of the first medical image acquired in step S10 and the size of the target region measured in step S24 (step S26).

Subsequently, in a case of creating the learning data, the learning data is sequentially stored in the memory 180 by repeating processing of step S10 to step S26.

Others

In the learning data creation apparatus and the method, the learning data is preferably created for each modality in a case where the modality capturing the first medical image varies. In addition, in a case where the modality is the endoscope system, individual learning data is preferably created in accordance with whether the endoscopic image is the normal light image or the special light image. Furthermore, individual learning data is preferably created in accordance with a type of endoscope-scope (an upper gastrointestinal endoscope, a lower gastrointestinal endoscope, a transnasal endoscope, a transoral endoscope, an endoscope having a varying angle of view, and the like).

In a case where the contact between the target region and the reference region is detected, the contact may be notified by voice or text.

Furthermore, the image display control unit 46A may not be disposed, and the medical image recognition apparatus 50 may display the recognition result such as the size information generated by the recognition result display control unit 46B in a superimposed manner on an image (the motion picture or the still picture) displayed by the endoscope processor apparatus 12.

While the endoscope processor apparatus 12 and the medical image recognition apparatus 50 are separately disposed in the embodiment, the endoscope processor apparatus 12 and the medical image recognition apparatus 50 may be integrated. That is, the endoscope processor apparatus 12 may be provided with a function as the medical image recognition apparatus 50.

Furthermore, a hardware structure for executing various controls of the learning data creation apparatus 100 and the medical image recognition apparatus 50 of the embodiment includes various processors illustrated as follows. Various processors include a central processing unit (CPU) that is a general-purpose processor functioning as various control units by executing software (program), a programmable logic device (PLD) such as a field programmable gate array (FPGA) that is a processor having a circuit configuration changeable after manufacturing, a dedicated electric circuit such as an application specific integrated circuit (ASIC) that is a processor having a circuit configuration dedicatedly designed to execute specific type of processing, and the like.

One processing unit may be configured with one of those various processors or may be configured with two or more processors of the same type or different types (for example, a plurality of FPGAs or a combination of a CPU and an FPGA). In addition, a plurality of control units may be configured with one processor. As an example of configuring the plurality of control units with one processor, first, as represented by a computer such as a client or a server, a form in which one processor is configured with a combination of one or more CPUs and software and this processor functions as the plurality of control units is available. Second, as represented by a system on chip (SoC) or the like, a form of using a processor that implements a function of the entire system including the plurality of control units by one integrated circuit (IC) chip is available. Accordingly, various control units are configured using one or more of those various processors as the hardware structure.

The present invention includes the learning data creation program that implements various functions as the learning data creation apparatus according to the embodiment of the present invention by installing the learning data creation program on a computer, and a recording medium on which the learning data creation program is recorded.

Furthermore, the present invention is not limited to the above embodiment and can be subjected to various modifications without departing from the spirit of the present invention.

EXPLANATION OF REFERENCES

9: endoscope system
10: endoscope-scope
11: light source apparatus
12: endoscope processor apparatus
13: display apparatus
14: second processor
15: operation unit
16: display
20: insertion part
21: hand operation unit
22: universal cord
25: flexible portion
26: bending portion
27: distal end portion
28: imaging element
29: bending operation knob
30: air supply and water supply button
31: suction button
32: still picture imaging instruction unit
33: treatment tool introduction port
35: light guide
36: signal cable
37a: connector
37b: connector
38: motion picture
38a: frame image
39: still picture
40: second medical image acquisition unit
41: CPU
42: size recognizer
43: target region recognizer
46: display control unit
46A: image display control unit
46B: recognition result display control unit
47: memory
50: medical image recognition apparatus
60: medical image
61: target region
100: learning data creation apparatus
101: first processor
102A: target region
102B: target region
104: reference region
110: first medical image acquisition unit
120: target region detection unit
130: reference region detection unit
140: contact determination unit
150: size measurement unit
160: size storage unit
170: storage control unit
180: memory
S1: size information
S2: rectangular frame
S10 to S26: step

What is claimed is:

1. A learning data creation apparatus comprising:
a first processor; and
a memory that stores learning data for machine learning,
wherein the first processor
acquires a first medical image from a modality from a time series of first medical images,
detects a target region from the acquired first medical image,
detects a reference region having a known size from the acquired first medical image,
determines whether or not the detected target region and the reference region are in contact,
measures a size of the target region based on the known size of the reference region in a case where a contact between the target region and the reference region is determined,
stores, in the memory, as the learning data, a pair of the first medical image including the target region and the measured size of the target region,
acquires another first medical image, from the time series of the first medical images, that is captured before or after the first medical image in which the contact between the target region and the reference region is determined and that includes the same target region as the target region included in the first medical image in which the contact is determined, and
stores, in the memory, as the learning data, a pair of the another first medical image and the measured size of the target region.

2. The learning data creation apparatus according to claim 1,
wherein the first processor stores, in the memory, the first medical image constituting the pair as input data and stores the size of the target region as answer data.

3. The learning data creation apparatus according to claim 1,
wherein the reference region is a region in which an artificial object is imaged.

4. The learning data creation apparatus according to claim 3,
wherein the artificial object is a treatment tool.

5. The learning data creation apparatus according to claim 3,
wherein in a case where a contact between the target region and the artificial object is detected based on image feature amounts of the target region and the reference region, the first processor determines that the reference region is in contact with the target region.

6. The learning data creation apparatus according to claim 3,
wherein in a case where a detection signal indicating a contact between the target region and the artificial object is input from a contact sensor that is arranged at a distal end of the artificial object and detects the contact, the first processor determines that the reference region is in contact with the target region.

7. The learning data creation apparatus according to claim 1,
wherein the first medical image stored as the learning data is an image, among a time series of first medical images, in which the contact between the target region and the reference region is determined.

8. A medical image recognition apparatus comprising:
a second processor including a size recognizer; and
a display or a speaker,
wherein the second processor
acquires a second medical image from a modality,
the size recognizer recognizes a size of a target region included in the second medical image in a case where the second medical image is input, and
notifies, by the display or the speaker, the size of the target region recognized by the size recognizer, and
the size recognizer
is subjected to machine learning processing using the learning data created by the learning data creation apparatus according to claim 1 and recognizes the size of the target region included in the second medical image in a case where the second medical image is input.

9. The medical image recognition apparatus according to claim 8,
wherein the size recognizer is a neural network on which the machine learning processing is performed using the learning data.

10. The medical image recognition apparatus according to claim 8,
wherein the second processor includes a target region recognizer into which the second medical image is input and that recognizes the target region included in the second medical image, and
the second processor notifies, by the display or the speaker, the size of the target region recognized by the size recognizer and positional information about the target region recognized by the target region recognizer.

11. A learning data creation method for creating learning data for machine learning and sequentially storing the created learning data in a memory by a first processor,
wherein each processing of the first processor includes
acquiring a first medical image from a modality from a time series of first medical images,
detecting a target region from the acquired first medical image,
detecting a reference region having a known size from the acquired first medical image,
determining whether or not the detected target region and the reference region are in contact,
measuring a size of the target region based on the known size of the reference region in a case where a contact between the target region and the reference region is determined,
storing, in the memory, as the learning data, a pair of the first medical image including the target region and the measured size of the target region,
acquiring another first medical image, among the time series of the first medical images, that is captured before or after the first medical image in which the contact between the target region and the reference region is determined and that includes the same target region as the target region included in the first medical image in which the contact is determined, and
storing, in the memory, as the learning data, a pair of the another first medical image and the measured size of the target region.

12. The learning data creation method according to claim 11,
wherein the reference region is a region in which an artificial object is imaged.

13. A non-transitory, computer-readable tangible recording medium which records thereon computer instructions that, when read by a computer, cause the computer to implement:
a function of acquiring a first medical image from a modality from a time series of first medical images;
a function of detecting a target region from the acquired first medical image;
a function of detecting a reference region having a known size from the acquired first medical image;
a function of determining whether or not the detected target region and the reference region are in contact;
a function of measuring a size of the target region based on the known size of the reference region in a case where a contact between the target region and the reference region is determined;
a function of storing, in the memory, as learning data for machine learning, a pair of the first medical image including the target region and the measured size of the target region;
a function of acquiring another first medical image, among the time series of the first medical images, that is captured before or after the first medical image in which the contact between the target region and the reference region is determined and that includes the same target region as the target region included in the first medical image in which the contact is determined; and
a function of storing, in the memory, as the learning data, a pair of the another first medical image and the measured size of the target region.

* * * * *